US005652356A

United States Patent [19]
Agrawal

[11] Patent Number: 5,652,356
[45] Date of Patent: Jul. 29, 1997

[54] INVERTED CHIMERIC AND HYBRID OLIGONUCLEOTIDES

[75] Inventor: Sudhir Agrawal, Shrewsbury, Mass.

[73] Assignee: Hybridon, Inc., Cambridge, Mass.

[21] Appl. No.: 516,454

[22] Filed: Aug. 17, 1995

[51] Int. Cl.$^6$ .......................... C07H 21/04; A61K 48/00
[52] U.S. Cl. ............................. 536/245; 536/25.3
[58] Field of Search ............... 536/24.5, 25.3; 514/44; 435/6

[56] References Cited

U.S. PATENT DOCUMENTS

| 4,806,463 | 2/1989 | Goodchild et al. | 435/5 |
| 5,149,797 | 9/1992 | Pederson et al. | 536/27 |
| 5,194,428 | 3/1993 | Agrawal et al. | 514/44 |

FOREIGN PATENT DOCUMENTS

| WO93/13121 | 7/1993 | WIPO . |
| 93/13740 | 7/1993 | WIPO . |
| 94/02498 | 2/1994 | WIPO . |
| 94/13685 | 6/1994 | WIPO . |
| 94/26887 | 11/1994 | WIPO . |
| 95/09236 | 4/1995 | WIPO . |

OTHER PUBLICATIONS

Monia et al. (1993) *The Journal of Biological Chemistry* 268:14514–14522.
Paterson et al., "Proc. Natl. Acad. Sci. USA 74", 4370–4374 (1977).
Zamecnik and Stephenson, "Proc. Natl. Acad. Sci. USA 75", 280–284 (1978).
Stephenson and Zamecnik, "Proc. Natl. Acad. Sci. USA 75", 285–288 (1978).
Agrawal, "Trends in Biotechnology 10", 152–158 (1992).
Tao et al., "Antisense Research and Development 5", 123–129 (1995).
Agrawal and Iyer, "Current Opinion in Biotechnology 6", 12–19 (1995).
Agrawal et al., "Clinical Pharmacokinetics 28", 7–16 (1995).
Zhang et al., "Clinical Pharmacology and Therapeutics 58", 44–53 (1995).
Krieg et al., "Nature 374", 546–549 (1995).
Galbraith et al., "Antisense Research and Development 4", 201–206 (1994).
Iyer et al., "Tetrahedron Asymmetry 6", 1051–1054 (1995).
Kandimalla et al., "Nucleosides and Nucleotides 14", 1031–1035 (1995).
Beaucage, "In Protocols for Oligonucleotides and Analogs: Synthesis and Properties", Agrawal (editor), pp. 33–62, Humana Press, Totowa, NJ (1993).
Agrawal & Goodchild, "Tet. Lett. 28", 3539–3542 (1987).
Kabat and Mayer (eds), "Experimental Immunochemistry, 2d Edition", 135–240, Springfield, IL, CC Thomas (1961).

*Primary Examiner*—George G. Elliott
*Assistant Examiner*—Scott W. Houtteman
*Attorney, Agent, or Firm*—Hale and Dorr LLP

[57] ABSTRACT

The invention relates to modified oligonucleotides that are useful for studies of gene expression and for the antisense therapeutic approach. The invention provides inverted hybrid oligonucleotides and inverted chimeric oligonucleotides, both of which produce reduced side effects, relative to traditional phosphorothioate, hybrid or chimeric oligonucleotides.

2 Claims, 8 Drawing Sheets

| | |
|---|---|
| Hyb108 | 5' CTC TCG CAC CCA UCU CUC UCC TTC T |
| Hyb109 | 5' CTC TCG CAC CCA UCU CUC UCC TTC T |
| Hyb110 | 5' CTC TCG CAC CCA UCU CUC TCC TTC T |
| Hyb111 | 5' CTC TCG CAC CCA UCU CUC TCC TTC T |
| Hyb112 | 5' CTC TCG CAC CCA UCU CUC TCC TTC T |
| Hyb113 | 5' CTC TCG CAC CCA UCU CUC TCC TTC T |
| Hyb114 | 5' CTC TCG CAC CCA UCU CTC TCC TTC T |
| Gem91-H | 5' CUC UCG CAC CCA TCT CTC TCC UUC U |
| Gem91 | 5' CTC TCG CAC CCA TCT CTC TCC TTC T |
| Gem91PO | 5' CTC TCG CAC CCA TCT CTC TCC TTC T |

*FIG. 1*

Hyb115    5' <u>CTC TCG</u> CAC CCA TCT CTC TCC TTC T 3'
Hyb116    5' CTC <u>TCG</u> CAC CCA TCT CTC TCC TTC <u>T</u> 3'
Hyb117    5' <u>CTC TCG</u> CAC CCA TCT CTC TCC TTC <u>T</u> 3'
Hyb118    5' CTC TCG CAC CCA TCT CTC TCC TTC <u>T</u> 3'
Hyb119    5' CTC TCG CAC <u>CCA</u> TCT CTC TCC TTC T 3'
Hyb120    5' CTC TCG CAC <u>CCA TCT</u> CTC TCC TTC T 3'
Hyb121    5' CTC TCG CAC CCA TCT CTC <u>TCC TTC</u> T 3'
Hyb122    5' <u>CTC</u> TCG CAC CCA TCT CTC <u>TCC TTC</u> T 3'
Hyb123    5' <u>CTC</u> TCG CAC CCA TCT CTC <u>TCC TTC T</u> 3'
Hyb124    5' <u>CTT CCT</u> CTC TCT ACC ACA <u>GCT CTC</u> T 3'

*FIG. 2*

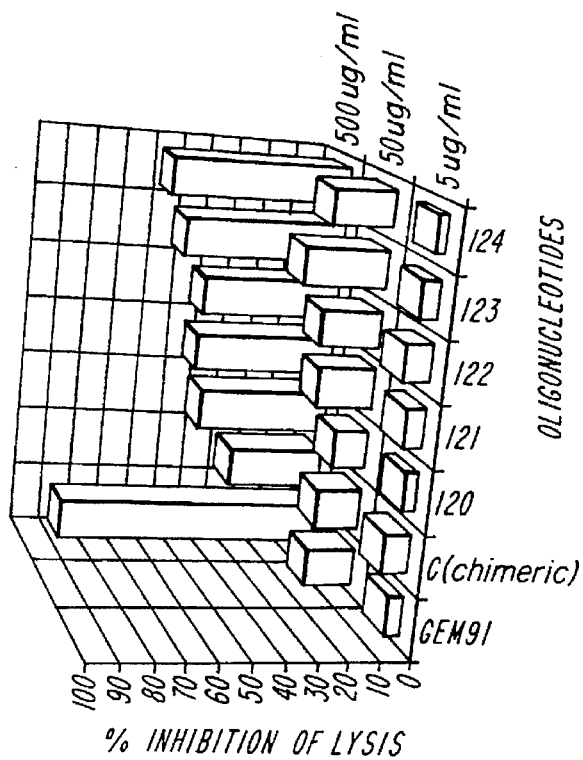
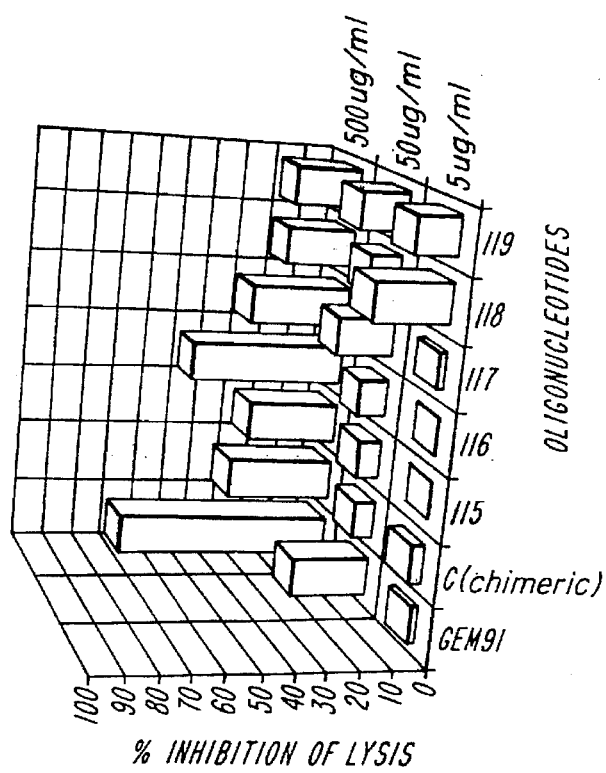
FIG. 7 of # INVERTED CHIMERIC AND HYBRID OLIGONUCLEOTIDES

BACKGROUND OF THE INVENTION

1. Field of the Invention

The invention relates to modified oligonucleotides that are useful for studies of gene expression and for the antisense therapeutic approach.

2. Summary of the Related Art

The potential for using oligonucleotides as inhibitors of specific gene expression in an antisense therapeutic approach was first suggested in three articles published in 1977 and 1978. Paterson et al., Proc. Natl. Acad. Sci. U.S.A. 74: 4370–4374 (1977) discloses that cell-free translation of mRNA can be inhibited by binding a complementary oligonucleotide to the mRNA. Zamecnik and Stephenson, Proc. Natl. Acad. Sci. U.S.A. 75: 280–284 and 285–288 (1978) disclose that a 13-mer synthetic oligonucleotide that is complementary to a part of the Rous sarcoma virus (RSV) genome can inhibit RSV replication in infected cell cultures and can inhibit RSV-mediated transformation of primary chick fibroblasts into malignant sarcoma cells.

Since these early studies, the ability of antisense oligonucleotides to inhibit virus propagation has become firmly established. U.S. Pat. No. 4,806,463 teaches that human immunodeficiency virus propagation can be inhibited by oligonucleotides that are complementary to any of various regions of the HIV genome. U.S. Pat. No. 5,194,428 discloses inhibition of influenza virus replication by phosphorothioate oligonucleotides complementary to the influenza virus polymerase 1 gene. Agrawal, Trends in Biotechnology 10: 152–158 (1992) reviews the use of antisense oligonucleotides as antiviral agents.

Antisense oligonucleotides have also been developed as anti-parasitic agents. PCT publication no. WO93/13740 discloses the use of antisense oligonucleotides to inhibit propagation of drug-resistant malarial parasites. Tao et al., Antisense Research and Development 5: 123–129 (1995) teaches inhibition of propagation of a schistosome parasite by antisense oligonucleotides.

More recently, antisense oligonucleotides have shown promise as candidates for therapeutic applications for diseases resulting from expression of cellular genes. PCT publication no. WO95/09236 discloses reversal of beta amyloid-induced neuronal cell line morphological abnormalities by oligonucleotides that inhibit beta amyloid expression. PCT publication no. WO94/26887 discloses reversal of aberrant splicing of a globin gene transcript by oligonucleotides complementary to certain portions of that transcript. PCT application no. PCT/US94/13685 discloses inhibition of tumorigenicity by oligonucleotides complementary to the gene encoding DNA methyltransferase.

The development of various antisense oligonucleotides as therapeutic and diagnostic agents has recently been reviewed by Agrawal and Iyer, Current Opinion in Biotechnology 6: 12–19 (1995).

As interest in the antisense therapeutic approach has grown, various efforts have been made to improve the pharmacologic properties of oligonucleotides by modifying the sugar-phosphate backbone. U.S. Pat. No. 5,149,797 describes traditional chimetic oligonucleotides having a phosphorothioate core region interposed between methylphosphonate or phosphoramidate flanking regions. PCT publication no. WO94/02498 discloses traditional hybrid oligonucleotides having regions of 2'-O-substituted ribonucleotides flanking a DNA core region.

Much is currently being discovered about the pharmacodynamic properties of oligonucleotides. Agrawal et al., Clinical Pharmacokinetics 28: 7–16 (1995) and Zhang et al., Clinical Pharmacology and Therapeutics 58: 44–53 (1995) disclose pharmacokinetics of anti-HIV oligonucleotides in human patients. Some of these new discoveries have led to new challenges to be overcome for the optimization of oligonucleotides as therapeutic agents. For example, Kniep et al., Nature 374: 546–549 (1995) discloses that oligonucleotides containing the CG dinucleotide flanked by certain other sequences have a mitogenic effect in vivo. Galbraith et al., Antisense Research and Development 4: 201–206 (1994) disclose complement activation by oligonucleotides. Henry et al., Pharm. Res. 11: PPDM8082 (1994) discloses that oligonucleotides may potentially interfere with blood clotting.

There is, therefor, a need for modified oligonucleotides that retain gene expression inhibition properties while producing fewer side effects than conventional oligonucleotides.

BRIEF SUMMARY OF THE INVENTION

The invention relates to modified oligonucleotides that are useful for studies of gene expression and for the antisense therapeutic approach. The invention provides modified oligonucleotides that inhibit gene expression and that produce fewer side effects than conventional oligonucleotides. In particular, the invention provides modified oligonucleotides that demonstrate reduced mitogenicity, reduced activation of complement and reduced antithrombotic properties, relative to conventional oligonucleotides.

In a first aspect, the invention provides inverted hybrid and inverted chimeric oligonucleotides and compositions of matter for inhibiting specific gene expression with reduced side effects. Such inhibition of gene expression can be used as an alternative to mutant analysis for determining the biological function of specific genes. Such inhibition of gene expression can also be used to therapeutically treat diseases that are caused by expression of the genes of a virus or a pathogen, or by the inappropriate expression of cellular genes.

In one preferred embodiment according to this aspect of the invention, the composition of matter comprises modified oligonucleotides having one or more 2'-O-substituted RNA region flanked by one or more oligodeoxyribonucleotide phosphorothioate region. In certain particularly preferred embodiments, the 2'-substituted RNA region is in between two oligodeoxyribonucleotide regions, a structure that is "inverted" relative to traditional hybrid oligonucleotides. In another preferred embodiment according to this aspect of the invention, the composition of matter comprises modified oligonucleotides having one or more nonionic oligonucleotide region flanked by one or more region of oligonucleotide phosphorothioate. In preferred embodiments, the nonionic region contains alkylphosphonate and/or phosphoramidate and/or phosphotriester internucleoside linkages. In certain particularly preferred embodiments, the nonionic oligonucleotide region is in between two oligonucleotide phosphorothioate regions, a structure that is "inverted" relative to traditional chimeric oligonucleotides.

In a second aspect, the invention provides a method for modulating gene expression in a mammal with reduced side effects. In the method according to this aspect of the invention, a composition of matter according to the first aspect of the invention is administered to the mammal, wherein the oligonucleotide is complementary to a gene that is being expressed in the mammal. In a preferred embodiment, after the composition of matter is administered, one or more measurement is taken of biological effects selected from the group consisting of complement activation, mitogenesis and inhibition of thrombin clot formation.

In a third aspect, the invention provides a method for therapeutically treating, with reduced side effects, a disease caused by aberrant gene expression, the method comprising administering to an individual having the disease a composition of matter according to the first aspect of the invention, wherein the oligonucleotide is complementary to a gene that is aberrantly expressed, wherein such aberrant expression causes the disease. In this context, aberrant gene expression means expression in a host organism of a gene required for the propagation of a virus or a prokaryotic or eukaryotic pathogen, or inappropriate expression of a host cellular gene. Inappropriate host cellular gene expression includes expression of a mutant allele of a cellular gene, or under-expression or overexpression of a normal allele of a cellular gene, such that disease results from such inappropriate host cellular gene expression. In a preferred embodiment, after the composition of matter is administered, one or more measurement is taken of biological effects selected from the group consisting of complement activation, mitogenesis and inhibition of thrombin clot formation.

BRIEF DESCRIPTION OF THE DRAWINGS

FIG. 1 shows inverted hybrid oligonucleotides, hybrid oligonucleotides and oligonucleotide phosphodiesters and phosphorothioates used in the current studies. 2'-O-methylribonucleotides are outlined and phosphodiester-linked nucleotides are underlined; all others are phosphorothioate-linked nucleotides.

FIG. 2 shows mixed backbone, chimeric and inverted chimeric oligonucleotides used in the current studies. Methylphosphonate-linked nucleotides are underlined; all others are phosphorothioate linked nucleotides.

FIG. 7 shows extent of inhibition of complement-mediated hemolysis observed when serum is treated with phosphorothioate oligonucleotide or any of various inverted chimetic oligonucleotides.

DETAILED DESCRIPTION OF THE PREFERRED EMBODIMENTS

Figure 3:
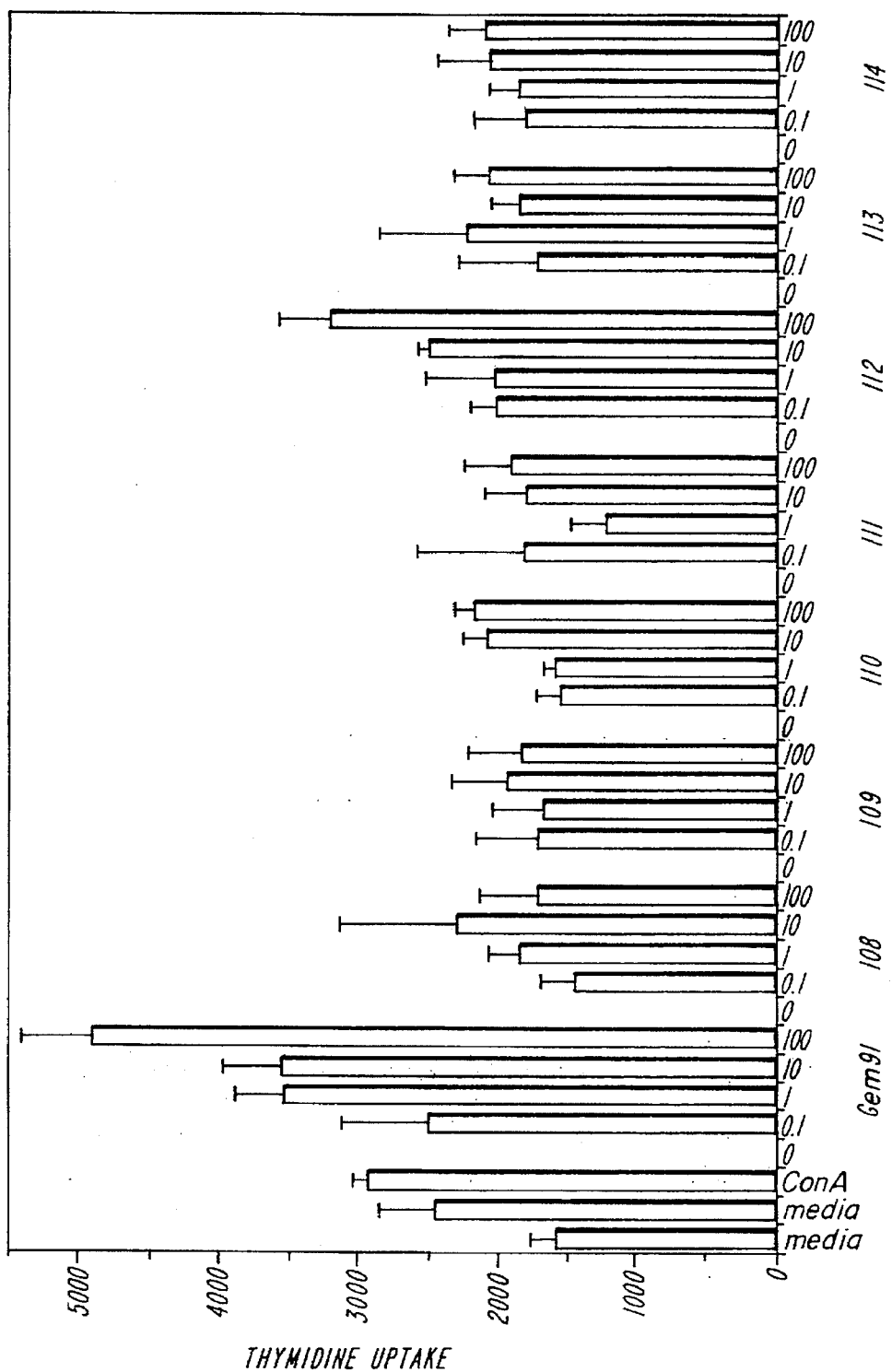
FIG. 3 shows thymidine uptake by mouse spleenocytes as a function of concentration of phosphorothioate oligonucleotide or any of various inverted hybrid oligonucleotides.
Figure 4:
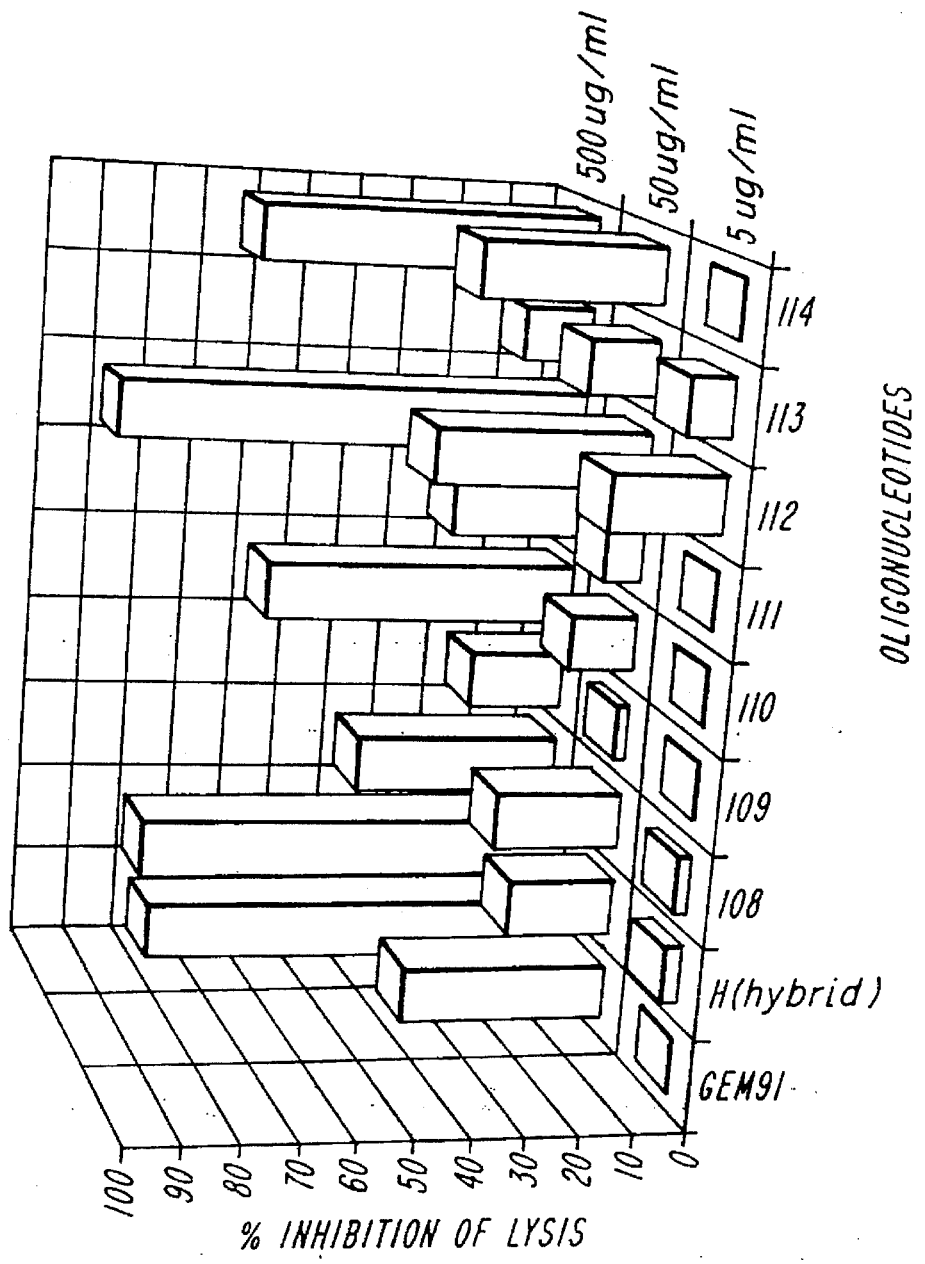
FIG. 4 shows extent of inhibition of complement-mediated hemolysis observed when serum is treated with phosphorothioate oligonucleotide or any of various inverted hybrid oligonucleotides.

All U.S. Patents, patent publications and scientific literature cited in this specification evidence the level of knowledge in the field and are hereby incorporated by reference.

The invention relates to modified oligonucleotides that are useful for studies of gene expression and for the antisense therapeutic approach. The invention provides modified oligonucleotides that inhibit gene expression and that produce fewer side effects than conventional oligonucleotides. In particular, the invention provides modified oligonucleotides that demonstrate reduced mitogenicity, reduced activation of complement and reduced antithrombotic properties, relative to conventional oligonucleotides.

In a first aspect, the invention provides inverted hybrid and inverted chimeric oligonucleotides and compositions of matter for inhibiting specific gene expression with reduced side effects. Such inhibition of gene expression can be used as an alternative to mutant analysis or gene "knockout" experiments for determining the biological function of specific genes. Such inhibition of gene expression can also be used to therapeutically treat diseases that are caused by expression of the genes of a virus or a pathogen, or by the inappropriate expression of cellular genes.

A composition of matter for inhibiting specific gene expression with reduced side effects, according to this aspect of the invention, comprises a modified oligonucleotide that is complementary to a portion of a genomic region or gene for which inhibition of expression is desired, or to RNA transcribed from such a gene. For purposes of the invention, the term oligonucleotide includes polymers of two or more deoxyribonucleotide, ribonucleotide, or 2'-O-substituted ribonucleotide monomers, or any combination thereof. The term oligonucleotide also encompasses such polymers having chemically modified bases or sugars and/or having additional substituents, including without limitation lipophilic groups, intercalating agents, diamines and adamantane. Preferably, such oligonucleotides will have from about 12 to about 50 nucleotides, most preferably from about 17 to about 35 nucleotides. The term complementary means having the ability to hybridize to a genomic region, a gene, or an RNA transcript thereof under physiological conditions. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization. As a practical matter, such hybridization can be inferred from the observation of specific gene expression inhibition. The gene sequence or RNA transcript sequence to which the modified oligonucleotide sequence is complementary will depend upon the biological effect that is sought to be modified. In some cases, the genomic region, gene, or RNA transcript thereof may be from a virus. Preferred viruses include, without limitation, human immunodeficiency virus (type 1 or 2), influenza virus, herpes simplex virus (type 1 or 2), Epstein-Barr virus, cytomegalovirus, respiratory syncytial virus, influenza virus, hepatitis B virus, hepatitis C virus and papilloma virus. In other cases, the genomic region, gene, or RNA transcript thereof may be from endogenous mammalian (including human) chromosomal DNA. Preferred examples of such genomic regions, genes or RNA transcripts thereof include, without limitation, sequences encoding vascular endothelial growth factor (VEGF), beta amyloid, DNA methyltransferase, protein kinase A, ApoE4 protein, p-glycoprotein, c-MYC protein, BCL-2 protein and CAPL. In yet other cases, the genomic region, gene, or RNA transcript thereof may be from a eukaryotic or prokaryotic pathogen including, without limitation, *Plasmodium falciparum, Plasmodium malarie, Plasmodium ovale*, Schistosoma spp., and *Mycobacterium tuberculosis*.

In addition to the modified oligonucleotide according to the invention, the composition of matter for inhibiting gene expression with reduced side effects may optionally contain any of the well known pharmaceutically acceptable carriers or diluents. This composition of matter may further contain one or more additional oligonucleotides according to the invention, which additional oligonucleotide may be either an inverted hybrid oligonucleotide or an inverted chimeric oligonucleotide. Alternatively, this composition may contain one or more traditional antisense oligonucleotide, such as an oligonucleotide phosphorthioate, a hybrid oligonucleotide, or a chimeric oligonucleotide, or it may contain any other pharmacologically active agent.

In one preferred embodiment according to this aspect of the invention, the composition of matter comprises modified oligonucleotides having one or more 2'-O-substituted RNA region flanked by one or more oligodeoxyribonucleotide phosphorothioate region. In certain particularly preferred embodiments, the 2'-O-substituted RNA region is in between two oligodeoxyribonucleotide phosphorothioate regions, a structure that is "inverted" relative to traditional hybrid oligonucleotides. Accordingly, oligonucleotides according to this embodiment are designated inverted hybrid oligonucleotides. The 2'-O-substituted RNA region preferably has from about four to about 10 or 13 2'-O-substituted nucleosides joined to each other by 5' to 3' internucleoside linkages, and most preferably from about four to about eight such 2'-O-substituted nucleosides. Preferably, the overall size of the inverted hybrid oligonucleotide will be from about 15 to about 35 or 50 nucleotides. Most preferably, the 2'-O-substituted ribonucleosides will be linked to each other through a 5' to 3' phosphorothioate, phosphotriester, or phosphodiester linkage. For purposes of the invention the term "2'-O-substituted" means substitution of the 2' position of the pentose moiety with an -O-lower alkyl group containing 1–6 saturated or unsaturated carbon atoms, or with an -O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group, but not with a 2'-H group. The phosphorothioate flanking region or regions has from about four to about 46 nucleosides joined to each other by 5' to 3' phosphorothioate linkages, and preferably from about 5 to about 26 such phosphorothioate-linked nucleosides. Most preferably, the phosphorothioate regions will have from about 5 to about 15 phosphorothioate-linked nucleosides. The phosphorothioate linkages may be mixed $R_p$ and $S_p$ enantiomers, or they may be stereoregular or substantially stereoregular in either $R_p$ or $S_p$ form (see Iyer et al., Tetrahedron Asymmetry 6: 1051–1054 (1995)).

In another preferred embodiment according to this aspect of the invention, the composition of matter comprises modified oligonucleotides having one or more nonionic oligonucleotide region flanked by one or more region of oligonucleotide phosphorothioate. In preferred embodiments, the nonionic region contains alkylphosphonate and/or phosphoramidate and/or phosphotriester internucleoside linkages. In certain particularly preferred embodiments, the nonionic oligonucleotide region is in between two oligonucleotide phosphorothioate regions, a structure that is "inverted" relative to traditional chimeric oligonucleotides. Accordingly, oligonucleotides according to this embodiment are designated inverted chimetic oligonucleotides. The nonionic region has from about four to about 10 or 12 nucleosides joined to each other by 5' to 3' nonionic linkages, preferably alkylphosphonate, phosphoramidate or phosphotriester linkages, and preferably from about four to about eight such nonionic-linked nucleosides. The phosphorothioate flanking region or regions has from about four to about 46 nucleosides joined to each other by 5' to 3' phosphorothioate linkages, and preferably from about eight to about 26 such phosphorothioate-linked nucleosides. Most preferably, the phosphorothioate regions will have from about 5 to about 15 phosphorothioate-linked nucleosides. The phosphorothioate linkages may be mixed $R_p$ and $S_p$ enantiomers, or they may be stereoregular or substantially stereoregular in either $R_p$ or $S_p$ form (see Iyer et al., Tetrahedron Asymmetry 6: 1051–1054 (1995). In a most preferred embodiment the oligonucleotide has a nonionic region having from about 6 to about 8 methylphosphonate-linked nucleosides, flanked on either side by phosphorothioate regions, each having from about 6 to about 10 phosphorothioate-linked nucleosides.

Those skilled in the art will recognize that the elements of these preferred embodiments can be combined and the inventor does contemplate such combination. For example, 2'-O-substituted ribonucleotide regions may well include from one to all nonionic internucleoside linkages. Alternatively, nonionic regions may have from one to all 2'-O-substituted ribonucleotides. Moreover, oligonucleotides according to the invention may contain combinations of one or more 2'-O-substituted ribonucleotide region and one or more nonionic region, either or both being flanked by phosphorothioate regions. (See Nucleosides & Nucleotides 14: 1031–1035 (1995) for relevant synthetic techniques.

In a second aspect, the invention provides a method for modulating gene expression in a mammal with reduced side effects. In the method according to this aspect of the invention, a composition of matter according to the first aspect of the invention is administered to the mammal, wherein the oligonucleotide is complementary to a gene that is being expressed in the mammal. Preferably, such administration may be parenteral, oral, intranasal or intrarectal. In a preferred embodiment, after the composition of matter is administered, one or more measurement is taken of biological side effects selected from the group consisting of complement activation, mitogenesis and inhibition of thrombin clot formation.

In a third aspect, the invention provides a method for therapeutically treating, with reduced side effects, a disease caused by aberrant gene expression, the method comprising administering to an individual having the disease a composition of matter according to the first aspect of the invention, wherein the oligonucleotide is complementary to a gene that is aberrantly expressed, wherein such aberrant expression causes the disease. In this context, aberrant gene expression means expression in a host organism of a gene required for the propagation of a virus or a prokaryotic or eukaryotic pathogen, or inappropriate expression of a host cellular gene. Inappropriate host cellular gene expression includes expression of a mutant allele of a cellular gene, or underexpression or overexpression of a normal allele of a cellular gene, such that disease results from such inappropriate host cellular gene expression. Preferably, such administration should be parenteral, oral, sublingual, transdermal, topical, intranasal or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may desirable to administer simultaneously, or sequentially a therapeutically effective amount of one or more of the therapeutic compositions of the invention to an individual as a single treatment episode. In a preferred embodiment, after the composition of matter is administered, one or more measurement is taken of biological effects selected from the group consisting of complement activation, mitogenesis and inhibition of thrombin clot formation.

The following examples are intended to further illustrate certain preferred embodiments of the invention and are not intended to limit the scope of the invention.

EXAMPLE 1

Synthesis, Deprotection And Purification Of Oligonucleotides

Oligonucleotide phosphorothioates were synthesized using an automated DNA synthesizer (Model 8700, Biosearch, Bedford, Mass.) using a beta-cyanoethyl phosphoramidite approach on a 10 micromole scale. To generate the phosphorothioate linkages, the intermediate phosphite linkage obtained after each coupling was oxidized using 3H, 1,2-benzodithiole-3H-one-1,1-dioxide (See Beaucage, In *Protocols for Oligonucleotides and Analogs: Synthesis and Properties*, Agrawal (editor), Humana Press, Totowa, N.J., pp. 33–62 (1993).) Similar synthesis was carried out to generate phosphodiester linkages, except that a standard oxidation was carried out using standard iodine reagent. Synthesis of inverted chimetic oligonucleotide was carried out in the same manner, except that methylphosphonate linkages were assembled using nucleoside methylphosphonamidite (Glen Research, Sterling, Va.), followed by oxidation with 0.1M iodine in tetrahydrofuran/2,6-lutidine/water (75:25:0.25) (see Agrawal & Goodchild, *Tet. Lett.* 28: 3539–3542 (1987). Inverted hybrid oligonucleotides were synthesized similarly, except that the segment containing 2'-O-methylribonucleotides was assembled using 2'-O-methylribonucleoside phosphoramidite, followed by oxidation to a phosphorothioate or phosphodiester linkage as described above. Deprotection and purification of oligonucleotides was carried out according to standard procedures, (See Padmapriya et al., Antisense Res. & Dev. 4: 185–199 (1994)), except for oligonucleotides containing methylphosphonate-containing regions. For those oligonucleotides, the CPG-bound oligonucleotide was treated with concentrated ammonium hydroxide for 1 hour at room temperature, and the supernatant was removed and evaporated to obtain a pale yellow residue, which was then treated with a mixture of ethylenediamine/ethanol (1:1 v/v) for 6 hours at room temperature and dried again under reduced pressure.

EXAMPLE 2

Reduced Complement Activation In Vitro By Inverted Hybrid And Inverted Chimetic Oligonucleotides To determine the relative effect of inverted hybrid or inverted chimeric structure on oligonucleotide-mediated depletion of complement, the following experiments were performed. Venous blood was collected from healthy adult human volunteers. Serum was prepared for hemolytic complement assay by collecting blood into vacutainers (Becton Dickinson #6430 Franklin Lakes, N.J.) without commercial additives. Blood was allowed to clot at room temperature for 30 minutes, chilled on ice for 15 minutes, then centrifuged at 4° C. to separate serum. Harvested serum was kept on ice for same day assay or, alternatively, stored at −70° C. Buffer, oligonucleotide phosphorothioate, inverted hybrid oligonucleotide, or inverted chimeric oligonucleotide was then incubated with the serum. A standard CH50 assay (see Kabat and Mayer (eds): *Experimental Immunochemistry*, 2d Edition, Springfield, Ill., C. C. Thomas (1961), p. 125) for complement-mediated lysis of sheep red blood cells (Colorado Serum Co.) sensitized with anti-sheep red cell antibody (hemolysin, Diamedix, Miami, Fla.) was performed, using duplicate determinations of at least five dilutions of each test serum, then hemoglobin release into cell-free supernates was measured spectrophotometrically at 541 nm.

EXAMPLE 3

Reduced Mitogenicity In Vitro Of Inverted Hybrid And Inverted Chimetic Oligonucleotides To determine the relative effect of inverted hybrid or inverted chimeric structure on oligonucleotide-mediated mitogenicity, the following experiments were performed. Spleen was taken from a male CD1 mouse (4–5 weeks, 20–22 g; Charles River, Wilmington, Mass.). Single cell suspensions were prepared by gently mincing with frosted edges of glass slides. Cells were then cultured in RPMI complete media [RPMI media supplemented with 10% fetal bovine serum (FBS), 50 micromolar 2-mercaptoethanol (2-ME), 100 U/ml penicillin, 100 micrograms/ml streptomycin, 2 mM L-glutamine]. To minimize oligonucleotide degradation, FBS was first heated for 30 minutes at 65° C. (phosphodiester-containing oligonucleotides) or 56° C. (all other oligonucleotides). Cells were plated in 96 well dishes at 100,000 cells per well (volume of 100 microliters/ well). Oligonucleotides in 10 microliters TE buffer (10 mM Tris-HCl, pH 7.5, 1 mM EDTA) were added to each well. After 44 hours of culturing at 37° C., one microcurie tritiated thymidine (Amersham, Arlington Heights, Ill.) was added in 20 microliters RPMI media for a 4 hour pulse labelling. The cells were then harvested in an automatic cell harvester (Skatron, Sterling, Va.) and the filters were assessed using a scintillation counter. In control experiments for mitogenicity, cells were treated identically, except that either media (negative control) or concanavalin A (positive control) was added to the cells in place of the oligonucleotides. The results of these studies are shown in FIG. 1. All of the inverted hybrid oligonucleotides proved to be less immunogenic than phosphorothioate oligonucleotides. Inverted hybrid oligonucleotides having phosphodiester linkages in the 2'-O-methyl region appeared to be slightly less immunogenic than those containing phosphorothioate linkages in that region. No significant difference in mitogenicity was observed when the 2'-O-methylribonucleotide region was pared down from 13 to 11 or to 9 nucleotides. Inverted chimeric oligonucleotides were also generally less mitogenic than phosphorothioate oligonucleotides. In addition, these oligonucleotides appeared to be less mitogenic than traditional chimetic oligonucleotides, at least in cases in which the traditional chimeric oligonucleotides had significant numbers of methylphosphonate linkages near the 3' end. Increasing the number of methylphosphonate linkers in the middle of the oligonucleotide from 5 to 6 or 7 did not appear to have a significant effect on mitogenicity. These results indicate that incorporation of inverted hybrid or inverted chimeric structure into an oligonucleotide can reduce its mitogenicity.

EXAMPLE 4

Figure 5:
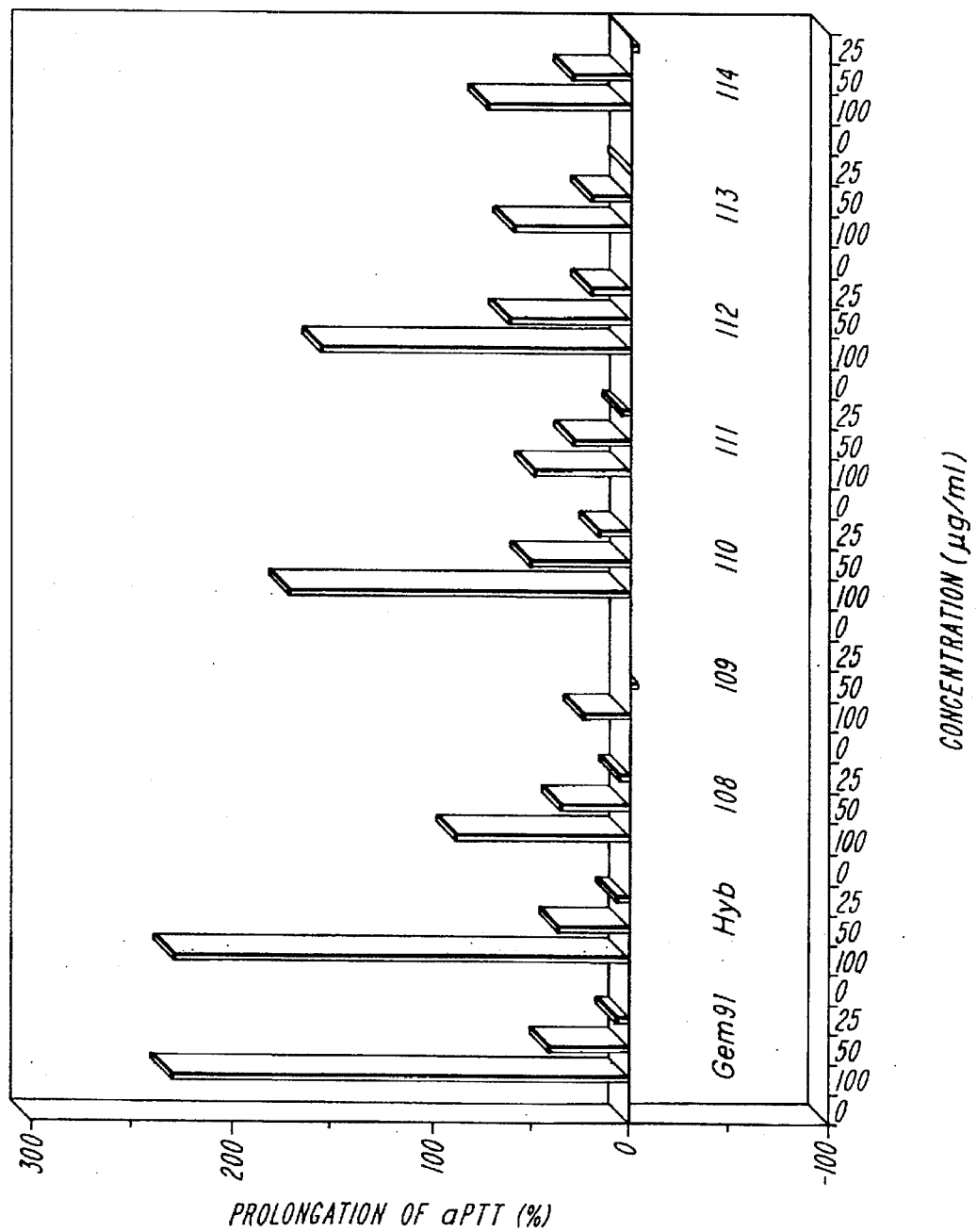
FIG. 5 shows prolongation of aPTT obtained when normal human serum is treated with phosphorothioate oligonucleotides or with any of various inverted hybrid oligonucleotides.
Figure 6:
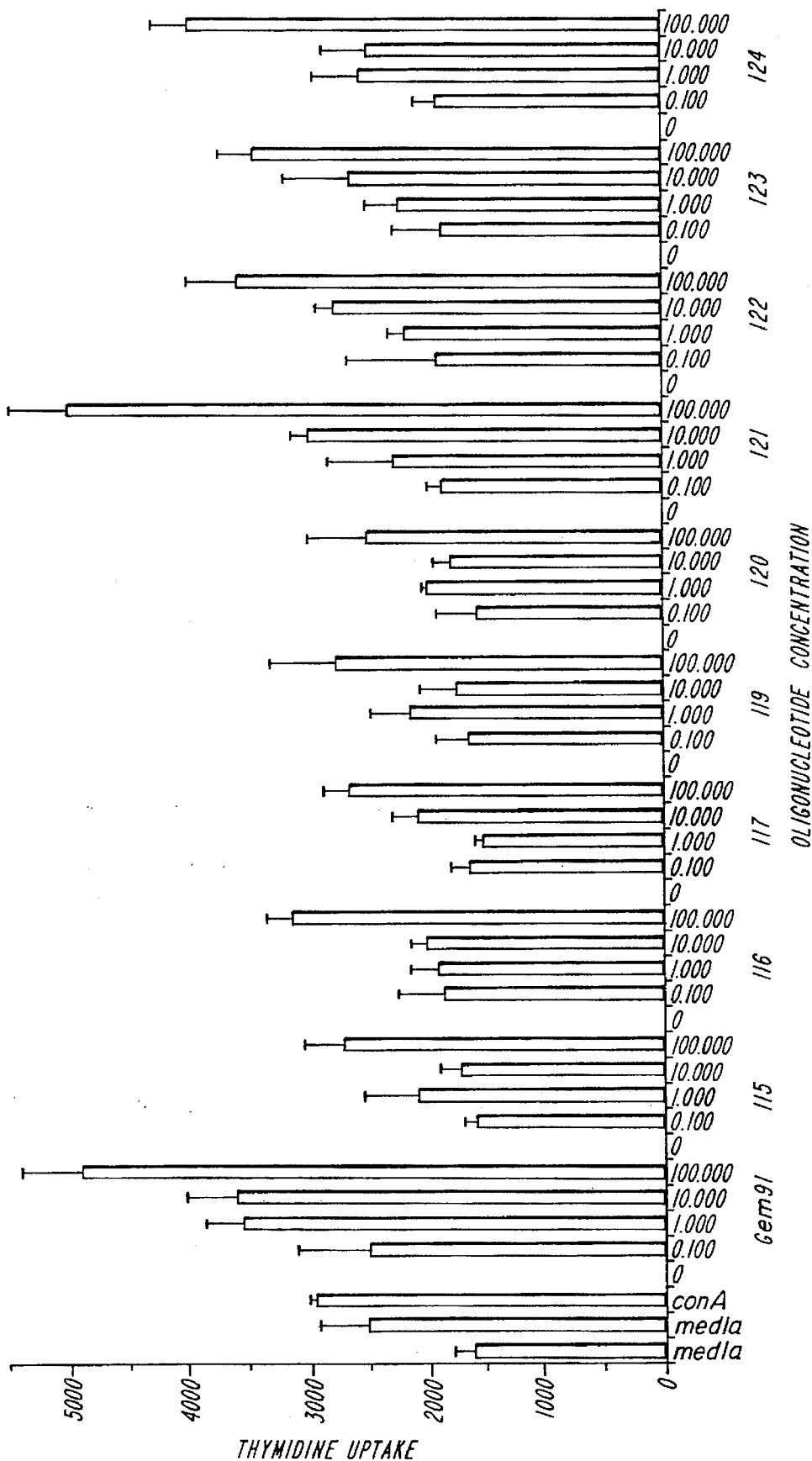
FIG. 6 shows thymidine uptake by mouse spleenocytes as a function of concentration of phosphorothioate oligonucleotide or any of various inverted chimeric oligonucleotides.
Figure 8:
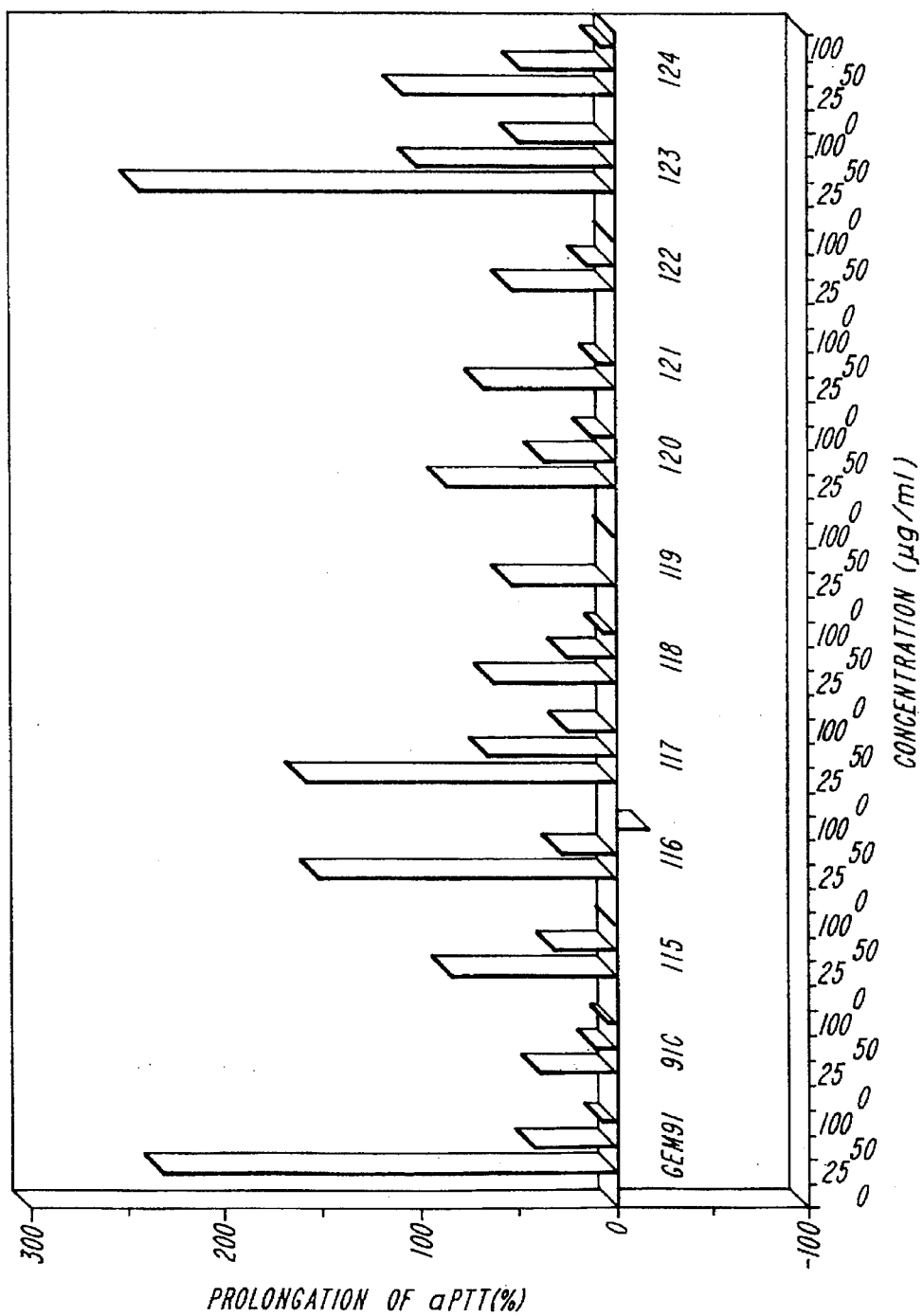
FIG. 8 shows prolongation of aPTT obtained when normal human serum is treated with phosphorothioate oligonucleotides or with any of various inverted chimeric oligonucleotides.

Reduced Inhibition Of Clotting In Vitro By Inverted Hybrid And Inverted Chimeric Oligonucleotides To determine the relative effect of inverted hybrid or inverted chimeric structure on oligonucleotide-induced mitogenicity, the following experiments were performed. Venous blood was collected from healthy adult human volunteers. Plasma for clotting time assay was prepared by collecting blood into siliconized vacutainers with sodium citrate (Becton Dickinson #367705), followed by two centifugations at 4° C. to prepare platelet-poor plasma. Plasma aliquots were kept on ice, spiked with various test compounds, and either tested immediately or quickly frozen on dry ice for subsequent storage at −20° C. prior to coagulation assay. Activated partial thromboplastin time (aPTT) was performed in duplicate on an Electra 1000 C (Medical Laboratory Automation, Mount Vernon, N.Y.) according to the manufacturer's recommended procedures, using Actin FSL (Baxter Dade, Miami, Fla.) and calcium to initiate clot formation, which was measured photometrically. Prolongation of aPTT was taken as an indication of clotting inhibition side effect produced by the oligonucleotide. The results are shown in FIG. 5 for inverted hybrid oligonucleotides and in FIG. 8 for inverted chimeric oligonucleotides. Traditional phosphorothioate oligonucleotides produce the greatest prolongation of aPTT, of all of the oligonucleotides tested. Traditional hybrid oligonucleotides produced somewhat reduced prolongation of aPTT. In comparison with traditional phosphorothioate or traditional hybrid oligonucleotides, all of the inverted hybrid oligonucleotides tested produced significantly reduced prolongation of aPTT. Inverted hybrid oligonucleotides having phosphodiester linkages in the 2'-O-substituted ribonucleotide region had the greatest reduction in this side effect, with one such oligonucleotide having a 2'-O-methyl RNA phosphodiester region of 13 nucleotides showing very little prolongation of aPTT, even at oligonucleotide concentrations as high as 100 micrograms/ml. Traditional chimeric oligonucleotides produce much less prolongation of aPTT than do traditional phosphorothioate oligonucleotides. Generally, inverted chimeric oligonucleotides retain this characteristic. At least one inverted chimetic oligonucleotide, having a methylphosphonate region of 7 nucleotides flanked by phosphorothioate regions of 9 nucleotides, gave better results in this assay than the traditional chimeric oligonucleotides at all but the highest oligonucleotide concentrations tested. These results indicate that inverted hybrid and inverted chimeric oligonucleotides may provide advantages in reducing the side effect of clotting inhibition when they are administered to modulate gene expression in vivo.

EXAMPLE 5

Reduced Complement Activation In Vivo By Inverted Hybrid And Inverted Chimeric Oligonucleotides Rhesus monkeys (4–9 kg body weight) are acclimatized to laboratory conditions for at least 7 days prior to the study. On the day of the study, each animal is lightly sedated with ketamine-HCl (10 mg/kg) and diazepam (0.5 mg/kg). Surgical level anasthesia is induced and maintained by continuous ketamine intravenous drip throughout the procedure. Phosphorothioate oligonucleotide or inverted hybrid or inverted chimeric oligonucleotide is dissolved in normal saline and infused intravenously via a cephalic vein catheter, using a programmable infusion pump at a delivery rate of 0.42 ml/minute. For each oligonucleotide, oligonucleotide doses of 0, 0.5, 1, 2, 5 and 10 mg/kg are administered to two animals each over a 10 minute infusion period. Arterial blood samples are collected 10 minutes prior to oligonucleotide administration and 2, 5, 10, 20, 40 and 60 minutes after the start of the infusion, as well as 24 hours later. Serum is used for determining complement CH50, using the conventional complement-dependent lysis of sheep ertyhrocyte procedure (see Kabat and Mayer, 1961, supra). At the highest dose, phosphorothioate oligonucleotide causes a decrease in serum complement CH50 beginning within 5 minutes of the start of infusion. Inverted hybrid and chimeric oligonucleotides are expected to show a much reduced or undetectable decrease in serum complement CH50 under these conditions.

EXAMPLE 6

Reduced Mitogenicity In Vivo Of Inverted Hybrid And Inverted Chimeric Oligonucleotides CD1 mice are injected intraperitoneally with a dose of 50 mg/kg body weight of phosphorothioate oligonucleotide, inverted hybrid oligonucleotide or inverted chimeric oligonucleotide. Forty-eight hours later, the animals are euthanized and the spleens are removed and weighed. Animals treated with inverted hybrid or inverted hybrid oligonucleotides are expected to show no significant increase in spleen weight, while those treated with oligonucleotide phosphorothioates are expected to show modest increases in spleen weight.

EXAMPLE 7

Reduced Inhibition Of Clotting In Vivo By Inverted Hybrid And inverted Chimetic Oligonucleotides Rhesus monkeys are treated as in example 5. From the whole blood samples taken, plasma for clotting assay is prepared, and the assay performed, as described in example 4. It is expected that prolongation of aPTT will be substantially reduced for both inverted hybrid oligonucleotides and for inverted chimetic oligonucleotides, relative to traditional oligonucleotide phosphorothioates.

EXAMPLE 8

Effect Of Inverted Hybrid Or Chimeric Structure On RNase H Activity

To determine the ability of inverted hybrid oligonucleotides and inverted chimetic oligonucleotides to actrate RNase H when bound to a complementary RNA molecule, the following experiments were performed. Each oligonucleotide phosphorothioate, inverted hybrid oligonucleotide or inverted chimeric oligonucleotide was incubated together with a molar equivalent quantity of complimentary oligoribonucleotide (0.266 micromolar concentration of each), in a cuvette containing a final volume of 1 ml RNase H buffer (20 mM Tris-HCl, pH 7.5, 10 mM $MgCl_2$, 0.1M KCl, 2% glycerol, 0.1 mM DTT). The samples were heated to 95° C., then cooled gradually to room temperature to allow annealing to form duplexes healed duplexes were incubated for 10 minutes at 37° C., then 5 units RNase H was added and data collection commenced over a three hour period. Data was collected using a GBC 920 (GBC Scientific Equipment, Victoria, Australia) spectrophotometer at 259 nm. RNase H degradation was determined by hyperchromic shift.

The results are shown in Table I, below.

TABLE I

RNase H Degradation Of Oligonucleotides

| Oligo No. (Features) | Half-Life | Oligo No. (Features) | Half-Life |
| --- | --- | --- | --- |
| GEM91 (all PO) | 8.8 sec | Hyb115 (5' MP) | 11.5 sec. |
| GEM91 (all PS) | 22.4 sec. | Hyb116 (chimeric) | 9.7 sec. |
| GEM91H (hybrid) | 32.7 sec. | Hyb117 (chimeric) | 8.1 sec. |
| Hyb108 (inv. hyb.) | 15.4 sec. | Hyb118 (inv. chim.) | 11.5 sec. |
| Hyb109 (inv. hyb.) | 7.9 sec. | Hyb119 (inv. chim.) | 14.4 sec. |
| Hyb110 (inv. hyb.) | 10.4 sec. | Hyb120 (inv. chim.) | 9.3 sec. |
| Hyb111 (inv. hyb.) | 12.9 sec. | Hyb121 (3' MP) | 21.2 sec. |
| Hyb112 (inv. hyb.) | 12.5 sec. | Hyb122 (chimeric) | 23.0 sec. |
| Hyb113 (inv. hyb.) | 10.9 sec. | Hyb123 (chimeric) | 41.8 sec. |
| Hyb114 (inv. hyb.) | 20.3 sec. | Hyb124 (chimeric) | not detect. |

As expected, phosphodiester oligonucleotides behaved as very good co-substrates for RNase H-mediated degradation of RNA, with a degradative half-life of 8.8 seconds. Phosphorothioate oligonucleotides produced an increased half-life of 22.4 seconds. Introduction of a 2'-O-methylribonucleotide segment at either end of the oligonucleotide further worsened RNaseH activity (half-life=32.7 seconds). In contrast, introducing a 2'-O-methyl segment into the middle of the oligonucleotide (inverted hybrid structure) always resulted in improved RNase H-mediated degradation. When a region of 13 2'-O-methylribonucleoside phosphodiesters was flanked on both sides by phosphorothioate DNA, the best RNase H activity was observed, with a half-life of 7.9 seconds. Introduction of large blocks of methylphosphonate-linked nucleosides at the 3' end of the oligonucleotide either had no effect or caused further deterioration of RNase H activity even when in a chimeric configuration. Introduction of methylphosphonate linked nucleosides at the 5' end, however, improved RNase H activity, particularly in a chimeric configuration with a single methylphosphonate linker at the 3' end (best half-life=8.1 seconds). All inverted chimetic oligonucleotides with methylphosphonate core regions flanked by phosphorothioate regions gave good RNase results, with a half-life range of 9.3 to 14.4 seconds. These results indicate that the introduction of inverted hybrid or inverted chimeric structure into phosphorothioate-containing oligonucleotides can restore some or all of the ability of the oligonucleotide to act as a co-substrate for RNase H, a potentially important attribute for an effective antisense agent.

EXAMPLE 9

Effect Of Inverted Hybrid Or Chimetic Structure On Melting Temperature

To determine the effect of inverted hybrid or inverted chimetic structure on stabilty of the duplex formed between an antisense oligonucleotide and a target molecule, the following experiments were performed. Thermal melting (Tm) data were collected using a GBC 920 spectrophotometer, which has six 10 mm cuvettes mounted in a dual carousel. In the Tm experiments, the temperature was directed and controlled through a peltier effect temperature controller by a computer, using software provided by GBC, according to the manufacturer's directions. Tm data were analyzed by both the first derivative method and the mid-point method, as performed by the software. Tm experiments were performed in a buffer containing 10 mM PIPES, pH 7.0, 1 mM EDTA, 1M NaCl. A VWR 1166 (VWR, Boston, Mass.) refrigerated bath was connected to the peltier-effect temperature controller to absorb the heat. Oligonucleotide strand concentration was determined using absorbance values at 260 nm, taking into account extinction coefficients.

The results are shown in Table II, below.

TABLE II

Duplex Stability Of Oligonucleotides

| Oligo No. (Features) | Tm (°C.)* | Oligo No. (Features) | Tm (°C.)* |
| --- | --- | --- | --- |
| GEM91 (all PO) | 72.0 | Hyb115 (5' MP) | 61.8 |
| GEM91 (all PS) | 63.6 | Hyb116 (chimeric) | 61.0 |
| GEM91H (hybrid) | 67.0 | Hyb117 (chimeric) | 60.5 |
| Hyb108 (inv. hyb.) | 76.4 | Hyb118 (inv. chim.) | 57.9 |
| Hyb109 (inv. hyb.) | 80.0 | Hyb119 (inv. chim.) | 57.7 |
| Hyb110 (inv. hyb.) | 74.2 | Hyb120 (inv. chim.) | 56.8 |
| Hyb111 (inv. hyb.) | 76.9 | Hyb121 (3' MP) | 60.7 |
| Hyb112 (inv. hyb.) | 72.1 | Hyb122 (chimeric) | 60.5 |
| Hyb113 (inv. hyb.) | 74.3 | Hyb123 (chimeric) | 59.0 |
| Hyb114 (inv. hyb.) | 71.3 | Hyb124 (chimeric) | not detect. |

*= with complementary RNA

These results demonstrate that conversion of a phosphodiester oligonucleotide to a phosphorothioate oligonucleotide results in a reduction of duplex stability, and that introduction of methylphosphonate linkages further reduces duplex stability. Duplex stabilty can be restored by adding 2'-O-methylribonucleotides, and can exceed that of the phosphodiester oligonucleotide when an inverted hybrid structure is used. Conversely, use of an inverted chimeric structure results in the lowest melting temperatures observed for any hybridizing methylphosphonate-containing oligonucleotide, although duplex stability was still well above physiological temperatures. Taken together, these results suggest that inverted hybrid or inverted chimeric structure can be used to custom design oligonucleotides for particular duplex stabilities desired in particular experimental or therapeutic applications.

What is claimed is:

1. A modified oligonucleotide having from about 15 to about 35 nucleotides, such modified oligonucleotide comprising a 2'-O-substituted RNA region in between two oligodeoxyribonucleotide phosphorothioate regions, wherein the 2'-O-substituted RNA region has from about 4 to about 13 phosphodiester-linked 2'-O-substituted ribonucleosides, each of which has a 2'-O-substitution selected from a hydroxy group, an amino group, a halo group and an —O-lower alkyl group containing 1–6 saturated or unsaturated carbon atoms or an —O-aryl or allyl group having 2–6 carbon atoms, wherein such alkyl, aryl or allyl group may be unsubstituted or may be substituted with halo, hydroxy, trifluoromethyl, cyano, nitro, acyl, acyloxy, alkoxy, carboxyl, carbalkoxyl, or amino groups; and wherein each of the oligodeoxyribonucleotide phosphorothioate regions has from about 5 to about 15 phosphorothioate-linked nucleosides.

2. A composition of matter for inhibiting gene expression with reduced side effects, the composition comprising the modified oligonucleotide according to claim 1.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 25 base pairs
( B ) TYPE: nucleic acid (C) STRANDEDNESS: single
       (D) TOPOLOGY: linear (ii) MOLECULE TYPE: Other nucleic acid (xi) SEQUENCE DESCRIPTION: SEQ ID NO:1:

CTCTCGCACC CAUCUCUCUC CTTCT 25

(2) INFORMATION FOR SEQ ID NO:2:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: Other nucleic acid (xi) SEQUENCE DESCRIPTION: SEQ ID NO:2:

CTCTCGCACC CAUCUCUCUC CTTCT 25

(2) INFORMATION FOR SEQ ID NO:3:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: Other nucleic acid (xi) SEQUENCE DESCRIPTION: SEQ ID NO:3:

CTCTCGCACC CAUCUCUCTC CTTCT 25

(2) INFORMATION FOR SEQ ID NO:4:

(i) SEQUENCE CHARACTERISTICS:
       (A) LENGTH: 25 amino acids
       (B) TYPE: nucleic acid
       (C) STRANDEDNESS: single
       (D) TOPOLOGY: linear (ii) MOLECULE TYPE: Other nucleic acid (xi) SEQUENCE DESCRIPTION: SEQ ID NO:4:

CTCTCGCACC CAUCUCUCTC CTTCT 25

(2) INFORMATION FOR SEQ ID NO:5:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (xi) SEQUENCE DESCRIPTION: SEQ ID NO:5:

CTCTCGCACC CAUCUCUCTC CTTCT 25

(2) INFORMATION FOR SEQ ID NO:6:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: Other nucleic acid (xi) SEQUENCE DESCRIPTION: SEQ ID NO:6:

CTCTCGCACC CAUCUCUCTC CTTCT                                              25

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:7:

CTCTCGCACC CAUCUCTCTC CTTCT                                              25

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:8:

CUCUCGCACC CATCTCTCTC CUUCU                                              25

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:9:

CTCTCGCACC CATCTCTCTC CTTCT                                              25

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:10:

CTCTCGCACC CATCTCTCTC CTTCT                                              25

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:11:

CTCTCGCACC CATCTCTCTC CTTCT                                              25

( 2 ) INFORMATION FOR SEQ ID NO:12:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:12:

CTCTCGCACC CATCTCTCTC CTTCT                   25

( 2 ) INFORMATION FOR SEQ ID NO:13:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:13:

CTCTCGCACC CATCTCTCTC CTTCT                   25

( 2 ) INFORMATION FOR SEQ ID NO:14:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:14:

CTCTCGCACC CATCTCTCTC CTTCT                   25

( 2 ) INFORMATION FOR SEQ ID NO:15:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:15:

CTCTCGCACC CATCTCTCTC CTTCT                   25

( 2 ) INFORMATION FOR SEQ ID NO:16:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:16:

CTCTCGCACC CATCTCTCTC CTTCT                   25

( 2 ) INFORMATION FOR SEQ ID NO:17:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:17:

CTCTCGCACC CATCTCTCTC CTTCT                                                                        25

( 2 ) INFORMATION FOR SEQ ID NO:18:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( i i ) MOLECULE TYPE: Other nucleic acid ( x i ) SEQUENCE DESCRIPTION: SEQ ID NO:18:

CTCTCGCACC CATCTCTCTC CTTCT                                                                        25

( 2 ) INFORMATION FOR SEQ ID NO:19:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( i i ) MOLECULE TYPE: Other nucleic acid ( x i ) SEQUENCE DESCRIPTION: SEQ ID NO:19:

CTCTCGCACC CATCTCTCTC CTTCT                                                                        25

( 2 ) INFORMATION FOR SEQ ID NO:20:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( i i ) MOLECULE TYPE: Other nucleic acid ( x i ) SEQUENCE DESCRIPTION: SEQ ID NO:20:

CTTCCTCTCT CTACCACAGC TCTCT                                                                        25